United States Patent [19]

Lee et al.

[11] Patent Number: 5,724,256
[45] Date of Patent: Mar. 3, 1998

[54] COMPUTER CONTROLLED OLFACTORY MIXER AND DISPENSER FOR USE IN MULTIMEDIA COMPUTER APPLICATIONS

[75] Inventors: Joseph Kinman Lee, Raleigh, N.C.; James Lee Lentz, Austin, Tex.; Ilya Iosephovich Novof, Essex Junction, Vt.

[73] Assignee: International Business Machines Corporation, Armonk, N.Y.

[21] Appl. No.: 661,271

[22] Filed: Jun. 10, 1996

[51] Int. Cl.$^6$ ........................................................ G06F 9/00
[52] U.S. Cl. ........................... 364/502; 364/509; 364/510; 364/479.11; 364/479.12; 422/5; 422/105; 422/110
[58] Field of Search ........................ 364/502, 138, 364/140, 509, 510, 131, 479.01, 479.03, 479.09, 479.1, 479.11, 479.12; 239/53–58, 145, 304; 392/390, 391, 393, 395; 422/5, 105, 110; 366/132, 138, 130, 315, 244, 220; 222/129.2, 132, 134, 136, 142.4, 142.5, 145.5, 145.6, 146.1–146.3, 146.5, 160, 165, 296; 141/99, 100, 110–112, 318, 285; 220/521, 577, 500, 503, 504, 529; 206/581; 434/377; 221/34, 9, 64, 65, 92, 93, 95, 96, 150 A, 197, 198

[56] References Cited

U.S. PATENT DOCUMENTS

| | | | |
|---|---|---|---|
| 1,546,302 | 7/1925 | Mehigan | 434/377 |
| 3,291,904 | 12/1966 | Ratliff, Jr. | 348/42 |
| 3,795,438 | 3/1974 | Westenholz et al. | 352/85 |
| 4,544,592 | 10/1985 | Spector | 428/68 |
| 4,582,492 | 4/1986 | Etter et al. | 434/236 |
| 4,629,604 | 12/1986 | Spector | 392/390 |
| 4,695,434 | 9/1987 | Spector | 239/56 |
| 4,747,782 | 5/1988 | Campbell, Jr. | 434/377 |
| 4,952,400 | 8/1990 | Tararuj et al. | 424/401 |
| 5,000,486 | 3/1991 | Rua, Jr. et al. | 283/102 |
| 5,018,974 | 5/1991 | Carnahan et al. | 434/98 |
| 5,175,791 | 12/1992 | Muderlak et al. | 392/390 |
| 5,431,885 | 7/1995 | Zlotnik et al. | 422/5 |
| 5,591,409 | 1/1997 | Watkins | 422/110 |

Primary Examiner—Emanuel T. Voeltz
Assistant Examiner—Hal D. Wachsman
Attorney, Agent, or Firm—Joseclyn G. Cockburn

[57] ABSTRACT

A computer controlled odor mixing and dispensing system has an linear array of odorant containers arranged in an annular member. Each container is provided with a computer controlled metering delivery device which dispenses the odorant onto a rotating absorptive porus member. An air handling system forces air through the rotating member which mixes the odors deposited thereon and delivers the mixed odors to a user.

8 Claims, 4 Drawing Sheets

OMDD = Odorant Metering Delivery Device

5,724,256

COMPUTER CONTROLLED OLFACTORY MIXER AND DISPENSER FOR USE IN MULTIMEDIA COMPUTER APPLICATIONS

FIELD OF THE INVENTION

This invention relates to computer controlled olfactory mixing dispensing system for use in multimedia computer applications and more particularly with computer controlled mixing and dispensing systems capable of generating a large number of different odors under computer program control using a limited number of selected scents.

BACKGROUND OF THE INVENTION

The desirability of using odors in conjunction with other means of disseminating information has been recognized for a long time. Any media which enhances realism is desirable, however, the improvement in realism and therefore total understanding must be effective and come at a reasonable cost.

U.S. Pat. No. 3,795,438 to Westenholtz et al discloses a mechanically controlled system for releasing an odor into an auditorium. U.S. Pat. No. 3,291,904 to Ratliff, Jr. discloses a stereophonic television system with an electro-mechanical odor releasing capability.

U.S. Pat. Nos. 4,952,400 to Tararuj et al., 4,544,592 to Spector, 5,018,974 to Carnahan et al., 4,747,782 to campbell, Jr., 5,000,486 to Rua, Jr. et al. and 1,546,302 to Mehigan all disclose various means for storing or encapsulating and mechanically releasing odor agents. U.S. Pat. No. 4,582,492 discloses a method for behavior modification using olfactory stimuli.

Computer controlled release of an associated odor in a computer controlled sales environment has been suggested.

SUMMARY OF THE INVENTION

The invention contemplates a computer controlled odor mixing and dispensing system suitable for use in conjunction with a multimedia computer application. An array of containers, each suitable for storing an odorant, is provided. Each container is fitted with a metering delivering device or the like, which under computer control can deliver a preselected quantity (0 to n) of the odorant stored in the container onto a moving absorption member. An air handling means establishes an air flow through the moving absorption member to delver the odorant mixture to a user.

DESCRIPTION OF THE PREFERRED EMBODIMENT

Figure 1:
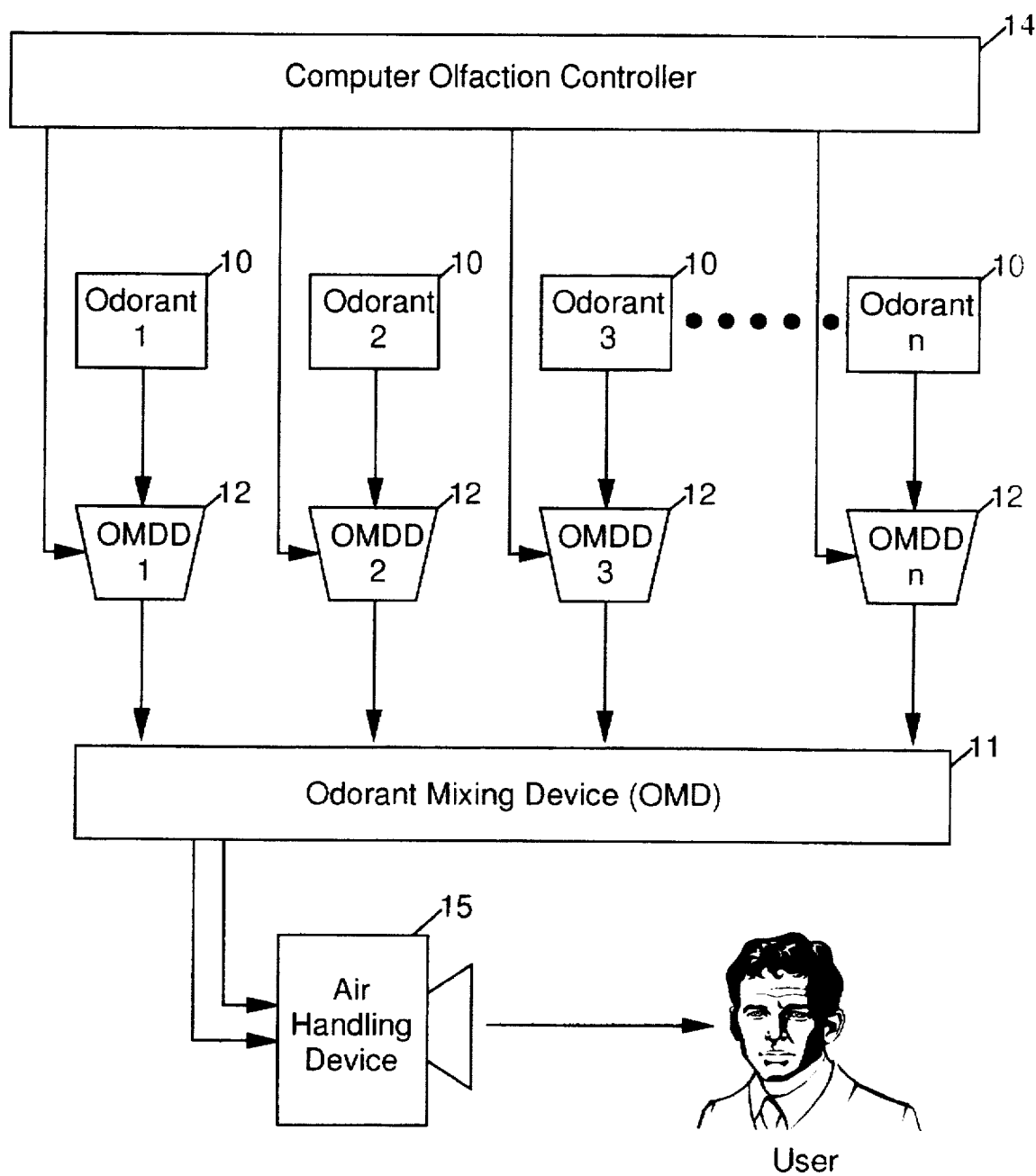
FIG. 1 is a schematic block diagram of a computer controlled odor mixing and dispensing system constructed according to the invention.

In FIG. 1, a plurality of storage containers 10, each suitable for storing a different odorant are in communication with an odorant mixing device 11 via one of a plurality of metering delivery devices 12. The metering delivery devices 12 are connected to a programmable control computer 14 which under program control can select the quantity of each of the odorants stored in containers 10 to be delivered to the mixing device 11. An air handling device 15 delivers the selectively mixed odorants to one or more users.

Figure 2:
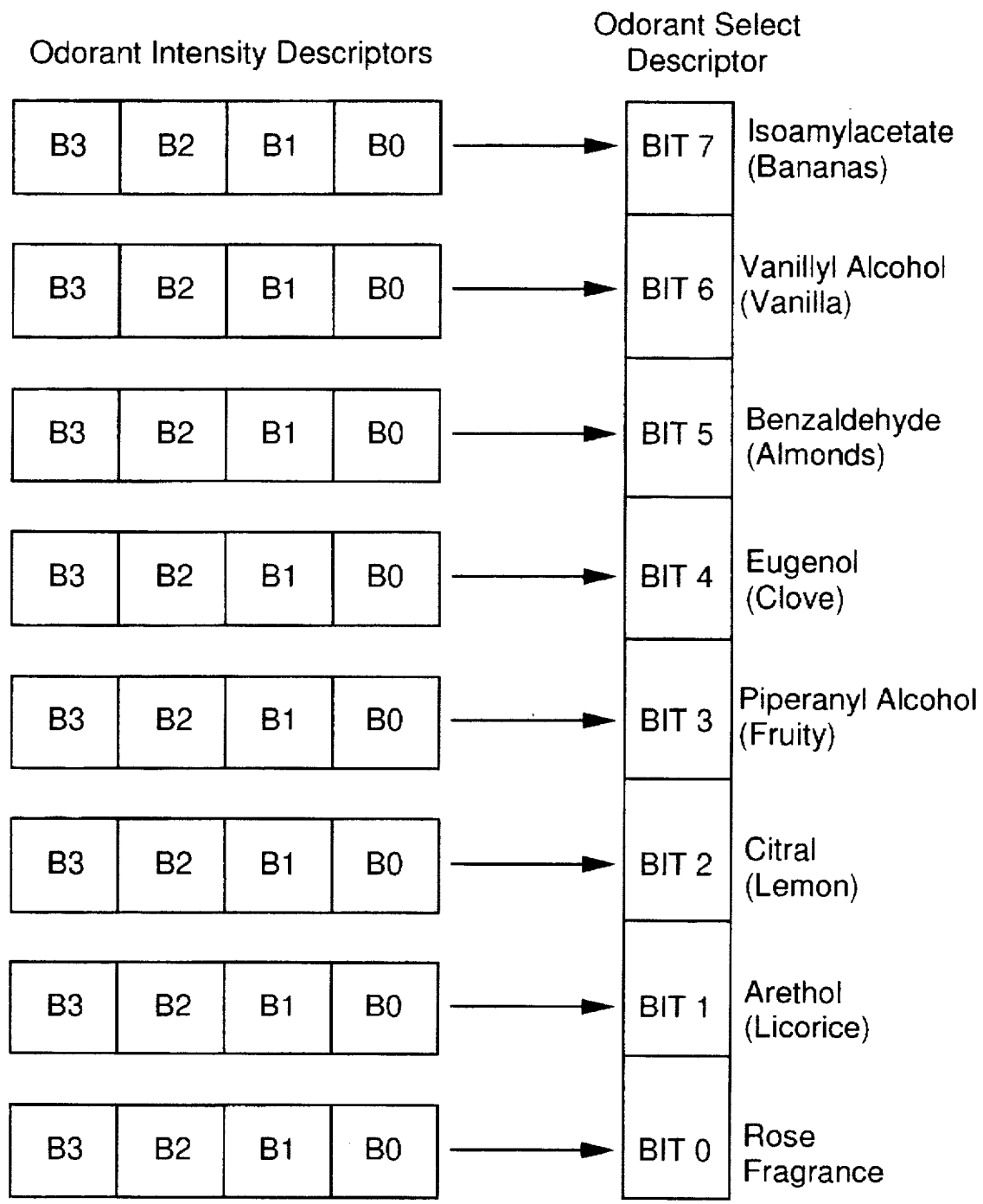
FIG. 2 is a schematic representation of the quantity selection architecture.

FIG. 2 illustrates an architecture for controlling the intensity of up to eight selected odors. Each bit of an odorant select descriptor is assigned to select, when set on, one of eight selected odorants. A four-bit odorant intensity descriptor is allocated to control the quantity of each of the eight selected odorants. With this architecture, up to eight odorants each having up to sixteen levels of intensity can be selected for delivery to the mixing device.

Figure 3:
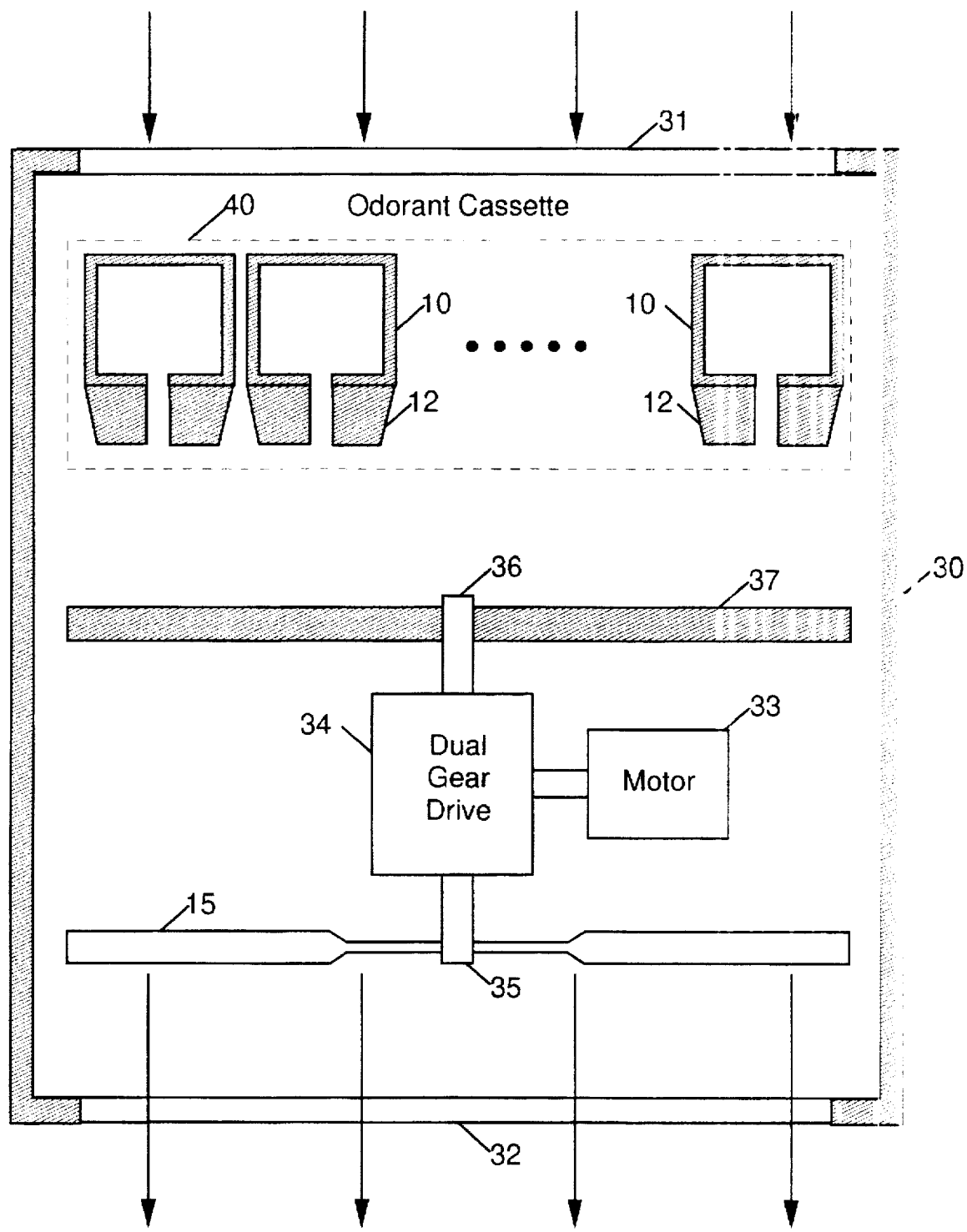
FIG. 3 is a diagram, in schematic cross section, of the mechanical and electro-mechanical components of the storage, metering delivery, mixing and delivery structures; and, FIG. 4 is a diagram similar to FIG. 3 illustrating a modification of the odorant storage structure.

In FIG. 3, the odorant mixing device 11 includes an annular member 30 which has top and bottom openings 31 and 32, respectively. The containers 10 and the associated metering delivery devices 12 are physically mounted inside annular member 30 near the top opening 31 and form a linear array. A motor 33 is connected to a dual speed gear drive 34. The motor 33 and dual speed gear drive 34 are supported within annular member 30 by a support structure not visible in the drawing.

A high speed output shaft 35 from dual speed gear drive 34 is connected to and drives a fan 15 at sufficiently high speed to cause an adequate air flow through annular member 30 from top to bottom. A second, low speed, output shaft 36 from dual speed gear drive 34 is connected to and drives a plane circular member 37. Member 37 is located below the linear array of metering delivery devices 12 and is constructed from a porus absorbent material.

As member 37 slowly rotates odorant agent droplets from selected and controlled delivering devices 12 are deposited on the porus absorbent material forming member 37. Turbulent air flow through annular member 30 causes a mixing of the odorants which are delivered to the user at the bottom opening of annular member 30.

Delivering devices 12 may be selected from different sources depending on the form of the odorant. If the odorant is a liquid, piezo electric pumps similar to those used in ink jet printers may be used. If the odorants are solids, heating elements can be used to vaporize discrete quantities as a function of current applied and the vapors absorbed in the member 37 are mixed in the air flow generated by the fan 15.

Figure 4:
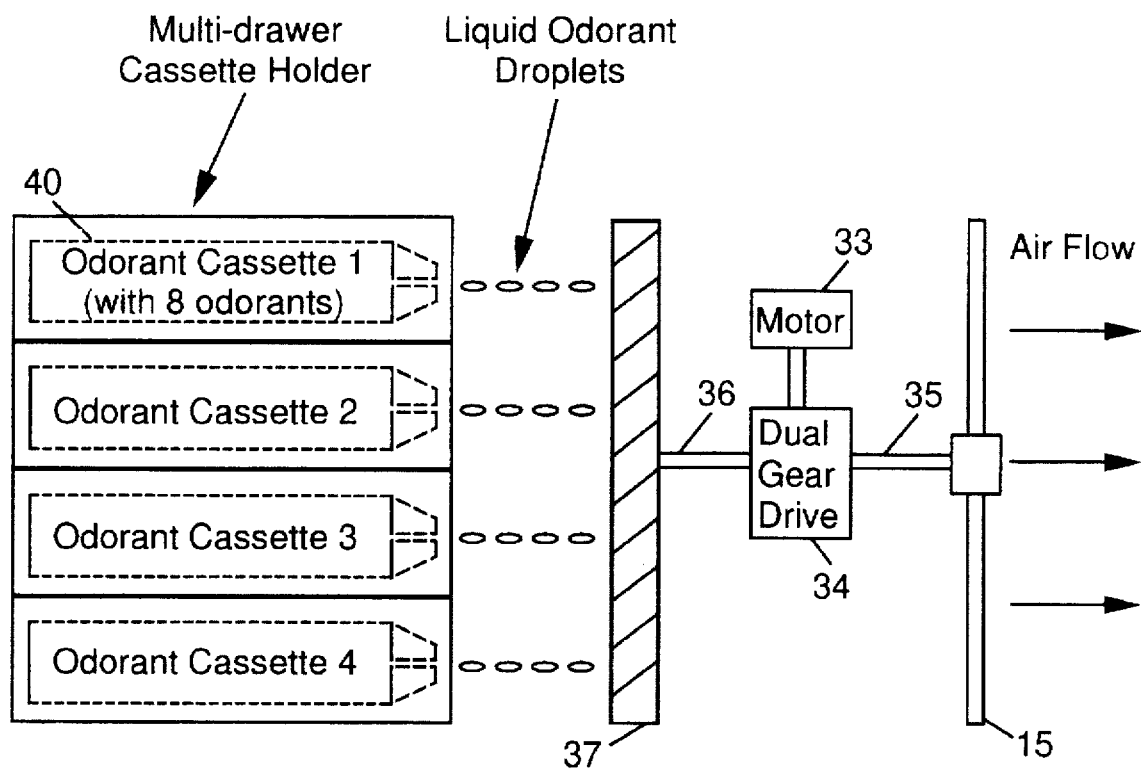

FIG. 4 illustrates a modification of the structure illustrated in FIG. 3. In those applications where a large number of different groups of odors are contemplated, each group of odorants can be stored in a cassette 40 of storage containers and associated metering delivery devices. The cassettes can be stacked within the annular member 30 of FIG. 3. The only modification to the selection architecture illustrated in FIG. 2 is the provision of a sufficient number of bits to select an appropriate cassette.

While several embodiments of the invention have been illustrated and described in detail, it will be clear to those skilled in this art that changes and modifications can be made without departing from the spirit and/or scope of the invention.

We claim:

1. A computer controlled odor mixing and dispensing system comprising:

a hollow member having at least one opening in each of two spaced surfaces to define a fluid inlet and a fluid outlet;

a plurality of containers each suitable for storing a different odorant arranged in an array and mounted in said hollow member proximate the opening defining the said fluid inlet;

a plurality of controllable delivering means, one connected to each of said plurality of containers, for controlling, in response to control signals supplied by a computer, the volume of odorant dispensed from its associated container;

a moving absorptive porus member mounted in said hollow member for receiving the odorants dispensed by said controllable metering delivery means; and, fluid pumping means mounted in said hollow member for establishing a fluid flow between said inlet and said outlet and through said moving absorptive porus member whereby odorants deposited on the said moving absorptive porus member are mixed by said fluid flow and motion and expelled at said fluid outlet.

2. A computer controlled odor mixing and dispensing system as set forth in claim 1 in which said hollow member is a cylinder and the fluid inlet and fluid outlet openings are located in the opposed planar end surfaces.

3. A computer controlled mixing and dispensing system as set forth in either claim 1 or claim 2 in which the odorant is a liquid and the controllable delivering means are piezoelectric pumps.

4. A computer controlled mixing and dispensing system as set forth in claim 3 in which the odorant containers are arranged in a linear array and the absorptive porus moving member is a slowly rotating disk.

5. A computer controlled mixing and dispensing system as set forth in claim 3 in which the odorant containers are arranged in a plurality of stacked cassettes and each cassette has a plurality of odorants.

6. A computer controlled mixing and dispensing system as set forth in either claim 1 or claim 2 in which the odorant is a solid and the controllable metering delivery means are heating elements for vaporizing the odorant as a function of a control current.

7. A computer controlled mixing and dispensing system as set forth in claim 6 in which the odorant containers are arranged in a linear array and the absorptive porus moving member is a slowly rotating disk.

8. A computer controlled mixing and dispensing system as set forth in claim 6 in which the odorant containers are arranged in a plurality of stacked cassettes and each cassette has a plurality of odorants.

* * * * *